(12) United States Patent
Guner et al.

(10) Patent No.: US 10,188,055 B1
(45) Date of Patent: Jan. 29, 2019

(54) WATERMELON LINE ACE PLUS

(71) Applicant: SAKATA SEED AMERICA, INC., Morgan Hill, CA (US)

(72) Inventors: Nihat Guner, Lehigh Acres, FL (US); Mohammed F. Hassan, Fort Myers, FL (US)

(73) Assignee: SAKATA SEED AMERICA, INC., Morgan Hill, CA (US)

( * ) Notice: Subject to any disclaimer, the term of this patent is extended or adjusted under 35 U.S.C. 154(b) by 0 days.

(21) Appl. No.: 15/678,371

(22) Filed: Aug. 16, 2017

(51) Int. Cl.
*A01H 1/02* (2006.01)
*A01H 1/04* (2006.01)
*A01H 3/00* (2006.01)
*A01H 5/08* (2018.01)
*A01H 5/10* (2018.01)
*A01H 6/34* (2018.01)
*C12N 5/04* (2006.01)

(52) U.S. Cl.
CPC .............. *A01H 5/08* (2013.01); *A01H 1/02* (2013.01); *A01H 1/04* (2013.01); *A01H 5/10* (2013.01); *A01H 6/342* (2018.05); *A01H 3/00* (2013.01)

(58) Field of Classification Search
CPC ........................................................ A01H 5/08
See application file for complete search history.

(56) References Cited

U.S. PATENT DOCUMENTS

| 5,523,520 | A | 12/1996 | Hunsperger et al. |
| 6,355,865 | B1 | 3/2002 | Elmstrom |
| 6,759,576 | B2 | 7/2004 | Zhang et al. |
| 7,071,374 | B2 | 7/2006 | Zhang et al. |
| 7,528,298 | B2 | 5/2009 | Zhang et al. |
| 7,550,652 | B2 * | 6/2009 | Zhang ............... A01H 5/08 800/260 |
| 8,034,999 | B2 | 10/2011 | Lanini et al. |
| 8,173,873 | B2 | 5/2012 | Zhang et al. |
| 8,212,118 | B1 | 7/2012 | Brusca et al. |
| 9,066,479 | B2 | 6/2015 | Bernier |
| 9,370,146 | B1 | 6/2016 | Bernier |
| 9,445,559 | B2 * | 9/2016 | Guner ............... A01H 5/08 |
| 2016/0150750 | A1 * | 6/2016 | Guner ............... A01H 5/08 800/265 |

OTHER PUBLICATIONS

Gunter et al (HortTechnology Oct. 2012 vol. 22 No. 5 694-699) (Year: 2012).*

Elmstrom, G. W. and Hopkins, D. L., 1981, Resistance of Watermelon Cultivars to Fusarium Wilt, Plant Disease, 65:825-827.
Eshed, et al., 1996, Less-than-additive epistatic interactions of quantitative trait loci in tomato, Genetics, 143:1807-1817.
Freeman, et al., 2007, Diploid watermelon pollenizer cultivars differ with respect to triploid watermelon yield, HortTechnology, 17(4) 518-522.
Freeman, et al., Revised 2013, Performance of selected diploid watermelon pollenizers, Horticultural Sciences Department, UF/IFAS Extension, document HS1081, original publication Jan. 2007.
Gunter, et al., 2012, Staminate flower production and Fusarium wilt reaction of diploid cultivars used as pollenizers for triploid watermelon, HortTechnology, 22(5) 694-699.
Kraft, et al., 2000, Linkage disequilibrium and fingerprinting in sugar beet, Theor. Appl. Genet., 101:323-326.
Martyn, R.D. and Netzer, D., 1991, Resistance to Races 0,1, and 2 of Fusarium Wilt of Watermelon in *Citrullus* sp. PI-296341-FR, HortScience, 26(4) 429-432.
Shipman, M., 2012, Pollenizer research should help seedless watermelon farmers, NC State News, obtained from https://news.ncsu.edu/2012/10/wms-gunter-watermelon/ on Feb. 13, 2015.
Wehner, T.C., 2008, Overview of the genes of watermelon, Proc. Cucurbitaceae 2008, EUCARPIA meeting, p. 79-89 (ed. M. Pitrat).
Wehner, T.C., 2008, Watermelon, In: J. Prohens and F. Nuez (eds.), Handbook of Plant Breeding; Vegetables I: Asteraceae, Brassicaceae, Chenopodiaceae, and Cucurbitaceae, Springer Science+Business LLC, New York, NY, pp. 368-405.
Sakata Vegetable Catalog 2016, published Aug. 17, 2016, cover page and pp. 82-88.
Sakata Watermelon Bulletin 2016, published Aug. 17, 2016, 4 pages.
Sakata Vegetables, Ace Plus Watermelon sheet, published Aug. 17, 2016, 1 page.

* cited by examiner

Primary Examiner — Lee A Visone
(74) Attorney, Agent, or Firm — Jondle & Associates, P.C.

(57) ABSTRACT

A watermelon cultivar, designated watermelon line Ace Plus, is disclosed. The invention relates to the seeds of watermelon line Ace Plus, to the plants of watermelon line Ace Plus and to methods for producing a watermelon plant by crossing the watermelon line Ace Plus with itself or another watermelon cultivar. The invention further relates to methods for producing triploid, seedless watermelon fruit using watermelon line Ace Plus as a parent of the pollenizer plant. This invention also relates to watermelon cultivars or breeding cultivars and plant parts derived from watermelon line Ace Plus, to methods for producing other watermelon cultivars, lines or plant parts derived from watermelon line Ace Plus and to the watermelon plants, varieties, and their parts derived from the use of those methods. The invention further relates to hybrid watermelon seeds, plants, and plant parts produced by crossing watermelon line Ace Plus with another watermelon cultivar.

31 Claims, No Drawings

WATERMELON LINE ACE PLUS

BACKGROUND OF THE INVENTION

The present invention relates to a new watermelon (*Citrullus lanatus*) cultivar designated watermelon line Ace Plus. All publications cited in this application are herein incorporated by reference.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include increased head size and weight, higher seed yield, improved color, resistance to diseases and insects, tolerance to drought and heat, and better agronomic quality.

Watermelon is a member of the Cucurbitaceae family and is a vine-like flowering plant thought to have originated in southern Africa. Watermelon is an annual plant with long, weak, trailing or climbing stems that is grown for its large edible fruit. The fruit has a thick rind and fleshy center that is red, orange, pink, yellow, green or white. The fruit is rich in vitamins A and C and can be eaten raw or cooked in various ways. There are over 1,200 varieties of watermelon worldwide, which range in weight from less than one to more than 90 kilograms.

Successful watermelon production depends on attention to various cultural practices. This involves soil management practices with special attention to proper fertilization, crop establishment with appropriate spacing, weed control, the introduction of bees for pollination, and suitable pollenizers for seedless watermelon, irrigation and pest management. Watermelon fruit size and shape; rind color; thickness and toughness; seed size, color and number; and flesh color, texture, soluble solids and freedom from fruit defects are all important characteristics to be considered in selection of watermelon varieties. In addition, seedless watermelons should be free of hard seeds and have undeveloped seeds that are small and innocuous.

Watermelon pollination is essential to the production of fruit. The flowers of watermelon plants are unisexual, with male and female flowers occurring on the same plant (monoecious). In order to set fruit, pollen from the male flower must be transferred to a female flower on that plant or another plant in the field. This pollen transfer is accomplished by several naturally occurring insects, but most effectively by the honeybee.

Seedless watermelon plants are triploid and are produced by crossing a tetraploid (2n=4x=44 chromosomes) inbred line as the female parent with a diploid (2n=2x=22) inbred line as the male parent of the hybrid; the resulting hybrid is a triploid (2n=3x=33). Triploid plants have three sets of chromosomes, and three sets cannot be divided evenly during meiosis. This results in nonfunctional female and male gametes although the flowers appear normal. Since the triploid hybrid is female sterile, the fruit induced by pollination tend to be seedless. As the pollen in triploid male flowers is not viable and female flowers in triploid plants require viable pollen to set fruit, it follows that there must be separate diploid (seeded) pollenizer plants available to provide pollen.

Triploid watermelon is mainly pollinated by bees and other insects that hop from flower to flower and distribute pollen from seeded pollenizer plants to triploid hybrid plants. Because watermelon flowers open only for a short time, it is essential that bees and pollens are present during pollination. It is also essential that the full-flowering period of the seedless plants (which takes about 3-4 weeks) should match with the full-flowering period of the pollenizer plants, in order to have plenty of pollen available during pollination. Lack of pollen during full flowering of seedless watermelon plants will have negative effect on the total yield and fruit quality. Therefore, early-maturing seedless watermelon hybrids should be combined with early and prolonged-flowering pollenizer plants to achieve high yield and quality watermelon production in commercial production fields.

Seeded watermelon plants take up space, nutrients and water in the field that farmers would rather devote to seedless plants. As a results, farmers have increasingly turned to varieties of seeded watermelons that produce pollen to fertilize the seedless plants, but that also grow very small, inedible fruit that does not need to be harvested and does not take up much space in the field. These varieties are called "pollenizers" because they are grown solely to provide pollen for the seedless watermelons.

Watermelon plants are susceptible to numerous diseases that attack the roots, foliage, and fruit. The most common diseases of watermelon are anthracnose, *fusarium* wilt, downy mildew, gummy stem blight, root-knot nematode and virus diseases. Disease control and production of resistant lines are thus essential for the production of high quality watermelons.

Therefore, developing improved inbred watermelon lines having early flowering, an increased number of flowers and an increased length of flowering period, producing an increased yield of marketable triploid fruit when used as a parent of a pollenizer, and having resistance to diseases, is highly desirable.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools, and methods which are meant to be exemplary and illustrative, not limiting in scope. In various embodiments, one or more of the above-described problems have been reduced or eliminated, while other embodiments are directed to other improvements.

According to the invention, there is provided a novel inbred watermelon cultivar designated watermelon line Ace Plus. This invention thus relates to the seeds of watermelon line Ace Plus, to the plants of watermelon line Ace Plus, and to methods for producing a watermelon plant produced by crossing the watermelon line Ace Plus with itself or another watermelon plant, to methods for producing a watermelon plant containing in its genetic material one or more transgenes, and to the transgenic watermelon plants produced by that method. This invention also relates to methods for producing other watermelon cultivars derived from watermelon line Ace Plus and to the watermelon cultivar derived by the use of those methods. This invention further relates to hybrid watermelon seeds and plants produced by crossing watermelon line Ace Plus with another watermelon variety, wherein watermelon line Ace Plus is used as the male and/or the female parent.

In another aspect, the present invention provides regenerable cells for use in tissue culture of watermelon line Ace Plus. The tissue culture will preferably be capable of regenerating plants having essentially all of the physiological and morphological characteristics of the foregoing watermelon plant, and of regenerating plants having substantially the same genotype as the foregoing watermelon plant. Preferably, the regenerable cells in such tissue cultures will be callus, protoplasts, meristematic cells, cotyledons, hypocotyl, leaves, pollen, embryos, roots, root tips, anthers, pistils, shoots, stems, petiole flowers, and seeds. Still further, the present invention provides watermelon plants regenerated from the tissue cultures of the invention.

Another aspect of the invention is to provide methods for producing other watermelon plants derived from watermelon line Ace Plus. Watermelon plants derived by the use of those methods are also part of the invention.

In another aspect, the present invention provides methods for producing triploid, seedless watermelon fruit when watermelon line Ace Plus is used as a parent of a diploid watermelon pollenizer plant. The method comprises planting a field with triploid watermelon plants and/or seeds; obtaining diploid pollenizer watermelon plants and/or seeds for pollinizing the triploid watermelon plants and/or seeds, wherein at least one parent of the diploid pollenizer plant is watermelon line Ace Plus; planting the pollenizer watermelon plants and/or seeds in the field of triploid watermelon plants and/or seeds; allowing pollination of the triploid watermelon plants by pollen of the pollenizer watermelon plants to obtain triploid, seedless watermelon fruit; and harvesting the triploid, seedless watermelon fruit. The planting and seedlings ratios of diploid to triploid plants were approximately equal to or less than 1 diploid pollenizer watermelon plant to 3, 4, 5, or 6 triploid watermelon plants.

The invention also relates to methods for producing a watermelon plant containing in its genetic material one or more transgenes and to the transgenic watermelon plant produced by those methods.

In another aspect, the present invention provides for single or multiple gene converted plants of watermelon line Ace Plus. The single or multiple transferred gene(s) may preferably be a dominant or recessive allele. Preferably, the single or multiple transferred gene(s) will confer such traits as male sterility, herbicide resistance, insect or pest resistance, modified fatty acid metabolism, modified carbohydrate metabolism, resistance for bacterial, fungal, or viral disease, male fertility, enhanced nutritional quality, and industrial usage. The single or multiple gene(s) may be a naturally occurring watermelon gene or a transgene introduced through genetic engineering techniques.

The invention further provides methods for developing watermelon plants in a watermelon plant breeding program using plant breeding techniques including recurrent selection, backcrossing, pedigree breeding, restriction fragment length polymorphism enhanced selection, genetic marker enhanced selection, and transformation. Seeds, watermelon plants, and parts thereof, produced by such breeding methods are also part of the invention.

In addition to the exemplary aspects and embodiments described above, further aspects and embodiments will become apparent by reference by study of the following descriptions.

DETAILED DESCRIPTION OF THE INVENTION

In the description and tables which follow, a number of terms are used. In order to provide a clear and consistent understanding of the specification and claims, including the scope to be given such terms, the following definitions are provided:

Allele. The "allele" is any of one or more alternative forms of a gene, all of which relate to one trait or characteristic. In a diploid cell or organism, the two alleles of a given gene occupy corresponding loci on a pair of homologous chromosomes.

Anthracnose. A destructive disease of watermelon caused by the fungus *Colletotrichum lagenarium* (Co), also known as *C. orbiculare*, which can infect all aboveground plant parts, especially during warm and moist conditions.

Backcrossing. "Backcrossing" is a process in which a breeder repeatedly crosses hybrid progeny back to one of the parents, for example, a first generation hybrid $F_1$ with one of the parental genotype of the $F_1$ hybrid.

Cotyledon. One of the first leaves of the embryo of a seed plant; typically one or more in monocotyledons, two in dicotyledons, and two or more in gymnosperms.

Cross-pollination. Fertilization by the union of two gametes from different plants.

Diploid. A cell or organism having two sets of chromosomes.

Essentially all the physiological and morphological characteristics. A plant having essentially all the physiological and morphological characteristics means a plant having the physiological and morphological characteristics of the recurrent parent, except for the characteristics derived from the converted gene.

Explosive rind. A trait (e) that causes the fruit rind of watermelon to burst or split when cut. Used to make fruit easily crushed by harvest crews for pollinator cultivars that have small fruit not intended for harvest.

*Fusarium* wilt. A major soilborne disease of watermelon caused by the fungus *Fusarium oxysporum* f. sp. *niveum* (Fon), which can result in significant damage to crop production.

Gene. As used herein, "gene" refers to a segment of nucleic acid. A gene can be introduced into a genome of a species, whether from a different species or from the same species, using transformation or various breeding methods.

Gene converted (conversion). "Gene converted" or "Single gene converted" (or conversion) plant refers to plants which are developed by a plant breeding technique called backcrossing wherein essentially all of the desired morphological and physiological characteristics of an inbred are recovered in addition to the one or more genes transferred into the inbred via the backcrossing technique or via genetic engineering.

Haploid. A cell or organism having one set of the two sets of chromosomes in a diploid.

Linkage. Refers to a phenomenon wherein alleles on the same chromosome tend to segregate together more often than expected by chance if their transmission was independent.

Locus. A defined segment of DNA.

Pedigree breeding/selection. "Pedigree breeding" is a breeding method used during the inbreeding of populations of self- and cross-pollinated species for the development of desirable homogeneous lines. Pedigree selection generally begins with an $F_2$ population and continues until homogeneous lines are developed.

Petiole. "Petiole" means the stalk of a leaf, attaching the leaf blade to the stem.

Plant. "Plant" includes plant cells, plant protoplasts, plant ovules, plant cells of tissue culture from which *C. lanatus* plants can be regenerated, plant calli, plant clumps and plant cells that are intact in plants, or parts of plants such as pollen, flowers, seeds, leaves, stems, fruit, rind, flesh and the like.

Pollenizer. Refers to diploid, seeded watermelon that produce pollen used to fertilize triploid, seedless watermelon plants and also grow very small, inedible fruit that does not need to be harvested.

Quantitative Trait Loci. "Quantitative Trait Loci" (QTL) refers to genetic loci that control to some degree, numerically representable traits that are usually continuously distributed.

Regeneration. "Regeneration" refers to the development of a plant from tissue culture.

RHS. "RHS" refers to the Royal Horticultural Society of England which publishes an official botanical color chart quantitatively identifying colors according to a defined numbering system. The chart may be purchased from Royal Horticulture Society Enterprise Ltd., RHS Garden; Wisley, Woking; Surrey GU236QB, UK.

Scion. Refers to a detached plant shoot containing buds, flowers or fruits that is used for grafting to stock or rootstock. The scion contains the desired genes to be duplicated in future production by the stock/scion plant.

Single gene converted. "Single gene converted" or "conversion plant" refers to plants which are developed by a plant breeding technique called backcrossing or via genetic engineering wherein essentially all of the desired morphological and physiological characteristics of a line are recovered in addition to the single gene transferred into the line via the backcrossing technique or via genetic engineering.

Stem. "Stem" means the above ground structures that have vascular tissue and that support, for example, leaves, flowers, seed, fruit, etc. The stem is normally divided into nodes and internodes, the nodes hold buds which grow into for example, one or more leaves, inflorescence (flowers), cones or other stems (or branches), while the internodes act as spaces that distance one node from another.

Tetraploid. A cell or organism having four sets of chromosomes.

Triploid. A cell or organism having three sets of chromosomes.

Yield. "Yield" means the total weight in kilograms of marketable harvested fruit from an experimental plot or field.

Watermelon line Ace Plus is an inbred diploid watermelon line with a small size, gray rind color, round oval, highly brittle rind, and red flesh fruit. Ace Plus has a very early flowering period and has resistance to Co:1 (Anthracnose) and Fon:1 (*Fusarium*). When compared to the closest commercial comparison varieties, watermelon line Ace Plus is earlier to flower and produces an increased number of male flowers having an increased length of male flowering period. Ace Plus also results in an increased yield of marketable triploid fruit when grown with this diploid pollenizer. Additionally, watermelon line Ace Plus has the explosive rind trait and a unique rind pattern.

Watermelon line Ace Plus has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in watermelon line Ace Plus.

Watermelon line Ace Plus has the following morphological and physiological characteristics (based primarily on data collected in Woodland, Calif.).

TABLE 1

| VARIETY DESCRIPTION INFORMATION |
|---|
| Plant: |
| Species: *Citrullus lanatus* var. *lanatus*<br>Adaptation: Most U.S. areas<br>Relative maturity: 70 days<br>Ploidy: Diploid |
| Stem: |
| Number of main stems at crown: 4, including stem holding fruit<br>Shape: Round<br>Diameter (at 2$^{nd}$ node): Not available<br>Surface: Pubescent |
| Leaf: |
| Shape: Ovate<br>Lobes: Lobed<br>Length: 18.0 cm<br>Width: 15.0 cm<br>Size: Longer than wide<br>Pubescence (both upper and lower surfaces): Pubescent<br>Color: |
| Upper surface: RHS 147A<br>Lower surface: RHS 147B |
| Flower: |
| Staminate flowers per plant at first fruit set: 8<br>Diameter across staminate: Not available<br>Color: Not available |
| Fruit: |
| General fruit type: Oblong, light green<br>Mature fruit shape: Oval<br>Length: 16.0 cm<br>Diameter at midsection: 14.0 cm<br>Average weight: 1514 g<br>Maximum weight: Not available<br>Surface: Smooth<br>Skin color pattern: Small stripe/mottle/net<br>Primary color: RHS 146D<br>Secondary color: RHS 146B |
| Rind: |
| Texture: Brittle<br>Penetrometer reading: Not available<br>Thickness (blossom end): 5.0 mm<br>Thickness (sides): 3.0 mm |
| Flesh: |
| Texture: Soft<br>Coarseness: Coarse fibrous<br>Color: RHS 179B (Greyed-red) |
| Seed: |
| Size: Large<br>Length: 1.2 cm<br>Width: 6.0 mm<br>Thickness: 2.0 mm<br>Number of seeds per fruit: 150<br>Color: RHS 200A |
| Disease resistance: |
| Fusarium wilt: Resistant<br>Anthracnose: Resistant |

This invention is also directed to methods for producing a watermelon plant by crossing a first parent watermelon plant with a second parent watermelon plant, wherein the first parent watermelon plant or second parent watermelon plant is the watermelon plant from watermelon line Ace Plus. Further, both the first parent watermelon plant and second parent watermelon plant may be from watermelon line Ace Plus. Therefore, any methods using watermelon line Ace Plus are part of this invention: selfing, backcrosses, hybrid breeding, and crosses to populations. Any plants produced using watermelon line Ace Plus as at least one parent are within the scope of this invention.

Additional methods include, but are not limited to, expression vectors introduced into plant tissues using a direct gene transfer method, such as microprojectile-mediated delivery, DNA injection, electroporation, and the like. More preferably, expression vectors are introduced into plant tissues by using either microprojectile-mediated delivery with a biolistic device or by using *Agrobacterium*-mediated transformation. Transformed plants obtained with the protoplasm of the invention are intended to be within the scope of this invention.

Further Embodiments of the Invention

Watermelon in general is an important and valuable vegetable crop. Thus, a continuing goal of watermelon plant breeders is to develop stable, high yielding watermelon cultivars that are agronomically sound. To accomplish this goal, the watermelon breeder must select and develop watermelon plants with traits that result in superior cultivars.

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer for special advertising and marketing, altered seed and commercial production practices, and new product utilization. The testing preceding release of a new cultivar should take into consideration research and development costs, as well as technical superiority of the final cultivar. For seed-propagated cultivars, it must be feasible to produce seed easily and economically.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, the overall value of the advanced breeding lines, and the number of successful cultivars produced per unit of input (e.g., per year, per dollar expended, etc.).

Promising advanced breeding lines are thoroughly tested and compared to appropriate standards in environments representative of the commercial target area(s) for at least three years. The best lines are candidates for new commercial cultivars. Those still deficient in a few traits are used as parents to produce new populations for further selection.

These processes, which lead to the final step of marketing and distribution, usually take from ten to twenty years from the time the first cross or selection is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of watermelon plant breeding is to develop new, unique, and superior watermelon cultivars and hybrids. The breeder initially selects and crosses two or more parental lines, followed by repeated selfing and selection, producing many new genetic combinations. The breeder can theoretically generate billions of different genetic combinations via crossing, selfing, and mutations. The breeder has no direct control at the cellular level. Therefore, two breeders will never develop the same line, or even very similar lines, having the same watermelon traits.

Each year, the plant breeder selects the germplasm to advance to the next generation. This germplasm is grown under different geographical, climatic, and soil conditions, and further selections are then made during, and at the end of, the growing season. The cultivars that are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same line twice by using the exact same original parents and the same selection techniques. This unpredictability results in the expenditure of large research monies to develop superior watermelon cultivars.

The development of commercial watermelon cultivars requires the development of watermelon varieties, the crossing of these varieties and selection of superior hybrid crosses. The hybrid seed is produced by manual crosses between selected male-fertile parents or by using male sterility systems. These hybrids are selected for certain single gene traits such as fruit color, flower color, pubescence color or herbicide resistance which indicate that the seed is truly a hybrid. Additional data on parental lines, as well as the phenotype of the hybrid, influence the breeder's decision whether to continue with the specific hybrid cross.

Pedigree breeding is used commonly for the improvement of self-pollinating crops or inbred lines of cross-pollinating crops. Two parents which possess favorable, complementary traits are crossed to produce an $F_1$. An $F_2$ population is produced by selfing one or several $F_1$'s or by intercrossing two $F_1$'s (sib mating). Selection of the best individuals is usually begun in the $F_2$ population. Then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines with each generation due to failure of some seeds to germinate or some plants to produce at least one seed. As a result, not all of the $F_2$ plants originally sampled in the population will be represented by a progeny when generation advance is completed.

In a multiple-seed procedure, watermelon breeders commonly harvest two or more seeds from the fruit of each plant in a population and bulk them to form a bulk sample. Part of the bulk is used to plant the next generation and part is put in reserve. The procedure has been referred to as modified single-seed descent or the "pod-bulk" (for bean crops) technique.

The multiple-seed procedure has been used to save labor at harvest. It is considerably faster to extract seeds with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

In addition to phenotypic observations, the genotype of a plant can also be examined. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs—which are also referred to as Microsatellites), and Single Nucleotide Polymorphisms (SNPs).

Isozyme Electrophoresis and RFLPs have been widely used to determine genetic composition. Shoemaker and Olsen (Molecular Linkage Map of Soybean (*Glycine max*), pp. 6.131-6.138 in S. J. O'Brien (ed.) *Genetic Maps: Locus Maps of Complex Genomes*, Cold Spring Harbor Laboratory Press, Cold Spring Harbor, N.Y. (1993)) developed a molecular genetic linkage map that consisted of 25 linkage groups with about 365 RFLP, 11 RAPD, three classical markers, and four isozyme loci. See also, Shoemaker, R. C., RFLP Map of Soybean, pp. 299-309, in Phillips, R. L. and Vasil, I. K. (eds.), *DNA-Based Markers in Plants*, Kluwer Academic Press, Dordrecht, the Netherlands (1994).

The invention further provides a method of determining the genotype of a plant of watermelon line Ace Plus, or a first generation progeny thereof, which may comprise obtaining a sample of nucleic acids from said plant and detecting in said nucleic acids a plurality of polymorphisms. This method may additionally comprise the step of storing the results of detecting the plurality of polymorphisms on a computer readable medium. The plurality of polymorphisms are indicative of and/or give rise to the expression of the morphological and physiological characteristics of watermelon line Ace Plus.

With any of the genotyping techniques mentioned herein, polymorphisms may be detected when the genotype and/or sequence of the plant of interest is compared to the genotype and/or sequence of one or more reference plants. The polymorphism revealed by these techniques may be used to establish links between genotype and phenotype. The polymorphisms may thus be used to predict or identify certain phenotypic characteristics, individuals, or even species. The polymorphisms are generally called markers. It is common practice for the skilled artisan to apply molecular DNA techniques for generating polymorphisms and creating markers. The polymorphisms of this invention may be provided in a variety of mediums to facilitate use, e.g. a database or computer readable medium, which may also contain descriptive annotations in a form that allows a skilled artisan to examine or query the polymorphisms and obtain useful information.

SSR technology is currently the most efficient and practical marker technology; more marker loci can be routinely used and more alleles per marker locus can be found using SSRs in comparison to RFLPs. For example, Diwan and Cregan described a highly polymorphic microsatellite locus in soybean with as many as 26 alleles. Diwan, N. and Cregan, P. B., *Theor. Appl. Genet.*, 95:22-225 (1997). SNPs may also be used to identify the unique genetic composition of the invention and progeny varieties retaining that unique genetic composition. Various molecular marker techniques may be used in combination to enhance overall resolution.

Molecular markers, which include markers identified through the use of techniques such as Isozyme Electrophoresis, RFLPs, RAPDs, AP-PCR, DAF, SCARs, AFLPs, SSRs, and SNPs, may be used in plant breeding. One use of molecular markers is Quantitative Trait Loci (QTL) mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent. This procedure attempts to minimize the amount of genome from the donor parent that remains in the selected plants. It can also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of germplasm as parental varieties or ancestors of a plant by providing a means of tracking genetic profiles through crosses.

Particular markers used for these purposes are not limited to the set of markers disclosed herein, but may include any type of marker and marker profile which provides a means of distinguishing varieties. In addition to being used for identification of watermelon line Ace Plus, a hybrid produced through the use of Ace Plus, and the identification or verification of pedigree for progeny plants produced through the use of Ace Plus, a genetic marker profile is also useful in developing a locus conversion of Ace Plus.

Means of performing genetic marker profiles using SNP and SSR polymorphisms are well known in the art. SNPs are genetic markers based on a polymorphism in a single nucleotide. A marker system based on SNPs can be highly informative in linkage analysis relative to other marker systems in that multiple alleles may be present.

Ace Plus and its plant parts can be identified through a molecular marker profile. Such plant parts may be either diploid or haploid. Also encompassed within the scope of the invention are plants and plant parts substantially benefiting from the use of Ace Plus in their development, such as Ace Plus comprising a locus conversion.

Molecular data from Ace Plus may be used in a plant breeding process. Nucleic acids may be isolated from a seed of Ace Plus or from a plant, plant part, or cell produced by growing a seed of Ace Plus, or from a seed of Ace Plus with a locus conversion, or from a plant, plant part, or cell of Ace Plus with a locus conversion. One or more polymorphisms may be isolated from the nucleic acids. A plant having one or more of the identified polymorphisms may be selected and used in a plant breeding method to produce another plant.

Mutation breeding is another method of introducing new traits into watermelon varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid, or acridines. Once a desired trait is observed through mutagenesis the trait may then be incorporated into existing germplasm by traditional breeding techniques. Details of mutation breeding can be found in *Principles of Cultivar Development* by Fehr, Macmillan Publishing Company (1993).

The production of double haploids can also be used for the development of homozygous varieties in a breeding program. Double haploids are produced by the doubling of a set of chromosomes from a heterozygous plant to produce a completely homozygous individual. For example, see Wan, et al., *Theor. Appl. Genet.*, 77:889-892 (1989).

Descriptions of other breeding methods that are commonly used for different traits and crops can be found in one of several reference books (e.g., *Principles of Plant Breeding*, John Wiley and Son, pp. 115-161 (1960); Allard (1960); Simmonds (1979); Sneep, et al. (1979); Fehr (1987); "Carrots and Related Vegetable Umbelliferae," Rubatzky, V. E., et al. (1999).

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Any DNA sequences, whether from a different species or from the same species, which are introduced into the genome using transformation or various breeding methods, are referred to herein collectively as "transgenes." Over the last fifteen to twenty years, several methods for producing transgenic plants have been developed, and the present invention, in particular embodiments, also relates to transformed versions of the claimed line.

Nucleic acids or polynucleotides refer to RNA or DNA that is linear or branched, single or double stranded, or a hybrid thereof. The term also encompasses RNA/DNA hybrids. These terms also encompass untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. Less common bases, such as inosine, 5-methylcytosine, 6-methyladenine, hypoxanthine, and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the invention may be produced by any means, including genomic preparations, cDNA preparations, in vitro synthesis, RT-PCR, and in vitro or in vivo transcription.

Plant transformation involves the construction of an expression vector that will function in plant cells. Such a vector comprises DNA comprising a gene under control of, or operatively linked to, a regulatory element (for example, a promoter). The expression vector may contain one or more such operably linked gene/regulatory element combinations. The vector(s) may be in the form of a plasmid, and can be used alone or in combination with other plasmids, to provide transformed watermelon plants using transformation methods as described below to incorporate transgenes into the genetic material of the watermelon plant(s).

Expression Vectors for Watermelon Transformation: Marker Genes

Expression vectors include at least one genetic marker, operably linked to a regulatory element (for example, a promoter) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which when placed under the control of plant regulatory signals confers resistance to kanamycin. Fraley, et al., *PNAS*, 80:4803 (1983). Another commonly used selectable marker gene is the hygromycin phosphotransferase gene which confers resistance to the antibiotic hygromycin. Vanden Elzen, et al., *Plant Mol. Biol.*, 5:299 (1985).

Additional selectable marker genes of bacterial origin that confer resistance to antibiotics include gentamycin acetyl transferase, streptomycin phosphotransferase, aminoglycoside-3'-adenyl transferase, the bleomycin resistance determinant. Hayford, et al., *Plant Physiol.*, 86:1216 (1988); Jones, et al., *Mol. Gen. Genet.*, 210:86 (1987); Svab, et al., *Plant Mol. Biol.*, 14:197 (1990); Hille, et al., *Plant Mol. Biol.*, 7:171 (1986). Other selectable marker genes confer resistance to herbicides such as glyphosate, glufosinate, or bromoxynil. Comai, et al., *Nature*, 317:741-744 (1985); Gordon-Kamm, et al., *Plant Cell*, 2:603-618 (1990); and Stalker, et al., *Science*, 242:419-423 (1988).

Selectable marker genes for plant transformation that are not of bacterial origin include, for example, mouse dihydrofolate reductase, plant 5-enolpyruvylshikimate-3-phosphate synthase, and plant acetolactate synthase. Eichholtz, et al., *Somatic Cell Mol. Genet.*, 13:67 (1987); Shah, et al., *Science*, 233:478 (1986); and Charest, et al., *Plant Cell Rep.*, 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include α-glucuronidase (GUS), α-galactosidase, luciferase and chloramphenicol, acetyltransferase. Jefferson, R. A., *Plant Mol. Biol.*, 5:387 (1987); Teeri, et al., *EMBO* 1, 8:343 (1989); Koncz, et al., *PNAS*, 84:131 (1987); and DeBlock, et al., *EMBO J.*, 3:1681 (1984).

In vivo methods for visualizing GUS activity that do not require destruction of plant tissues are available. Molecular Probes, Publication 2908, IMAGENE GREEN, pp. 1-4 (1993) and Naleway, et al., *J. Cell Biol.*, 115:151a (1991). However, these in vivo methods for visualizing GUS activity have not proven useful for recovery of transformed cells because of low sensitivity, high fluorescent backgrounds, and limitations associated with the use of luciferase genes as selectable markers.

More recently, a gene encoding Green Fluorescent Protein (GFP) has been utilized as a marker for gene expression in prokaryotic and eukaryotic cells. Chalfie, et al., *Science*, 263:802 (1994). GFP and mutants of GFP may be used as screenable markers.

Expression Vectors for Watermelon Transformation: Promoters

Genes included in expression vectors must be driven by a nucleotide sequence comprising a regulatory element (for example, a promoter). Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters which initiate transcription only in certain tissue are referred to as "tissue-specific." A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters:

An inducible promoter is operably linked to a gene for expression in watermelon. Optionally, the inducible promoter is operably linked to a nucleotide sequence encoding a signal sequence which is operably linked to a gene for expression in watermelon. With an inducible promoter, the rate of transcription increases in response to an inducing agent.

Any inducible promoter can be used in the instant invention. See Ward, et al., *Plant Mol. Biol.*, 22:361-366 (1993). Exemplary inducible promoters include, but are not limited to, that from the ACEI system which responds to copper (Meft, et al., *PNAS*, 90:4567-4571 (1993)); In2 gene from maize which responds to benzenesulfonamide herbicide safeners (Hershey, et al., *Mol. Gen. Genet.*, 227:229-237 (1991) and Gatz, et al., *Mol. Gen. Genet.*, 243:32-38 (1994)) or Tet repressor from Tn10 (Gatz, et al., *Mol. Gen. Genet.*, 227:229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena, et al., *PNAS*, 88:0421 (1991).

B. Constitutive Promoters:

A constitutive promoter is operably linked to a gene for expression in watermelon or the constitutive promoter is operably linked to a nucleotide sequence encoding a signal sequence which is operably linked to a gene for expression in watermelon.

Many different constitutive promoters can be utilized in the instant invention. Exemplary constitutive promoters include, but are not limited to, the promoters from plant viruses such as the 35S promoter from CaMV (Odell, et al., *Nature*, 313:810-812 (1985)) and the promoters from such genes as rice actin (McElroy, et al., *Plant Cell*, 2:163-171 (1990)); ubiquitin (Christensen, et al., *Plant Mol. Biol.*, 12:619-632 (1989) and Christensen, et al., *Plant Mol. Biol.*, 18:675-689 (1992)); pEMU (Last, et al., *Theor. Appl. Genet.*, 81:581-588 (1991)); MAS (Velten, et al., *EMBO J.*, 3:2723-2730 (1984)) and maize H3 histone (Lepetit, et al., *Mol.*

Gen. Genet., 231:276-285 (1992) and Atanassova, et al., Plant J., 2 (3):291-300 (1992)). The ALS promoter, XbaI/NcoI fragment 5' to the *Brassica napus* ALS3 structural gene (or a nucleotide sequence similarity to said XbaI/NcoI fragment), represents a particularly useful constitutive promoter. See PCT Application No. WO 96/30530.

C. Tissue-Specific or Tissue-Preferred Promoters:

A tissue-specific promoter is operably linked to a gene for expression in watermelon. Optionally, the tissue-specific promoter is operably linked to a nucleotide sequence encoding a signal sequence which is operably linked to a gene for expression in watermelon. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai, et al., Science, 23:476-482 (1983) and Sengupta-Gopalan, et al., PNAS, 82:3320-3324 (1985)); a leaf-specific and light-induced promoter such as that from cab or rubisco (Simpson, et al., EMBO J., 4(11):2723-2729 (1985) and Timko, et al., Nature, 318:579-582 (1985)); an anther-specific promoter such as that from LAT52 (Twell, et al., Mol. Gen. Genet., 217:240-245 (1989)); a pollen-specific promoter such as that from Zm13 (Guerrero, et al., Mol. Gen. Genet., 244:161-168 (1993)) or a microspore-preferred promoter such as that from apg (Twell, et al., Sex. Plant Reprod., 6:217-224 (1993)).

Signal Sequences for Targeting Proteins to Subcellular Compartments

Transport of protein produced by transgenes to a subcellular compartment such as the chloroplast, vacuole, peroxisome, glyoxysome, cell wall, or mitochondrion, or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example, Becker, et al., Plant Mol. Biol., 20:49 (1992); Close, P. S., Master's Thesis, Iowa State University (1993); Knox, C., et al., "Structure and Organization of Two Divergent Alpha-Amylase Genes from Barley," Plant Mol. Biol., 9:3-17 (1987); Lerner, et al., Plant Physiol., 91:124-129 (1989); Fontes, et al., Plant Cell, 3:483-496 (1991); Matsuoka, et al., PNAS, 88:834 (1991); Gould, et al., J. Cell. Biol., 108:1657 (1989); Creissen, et al., Plant J., 2:129 (1991); Kalderon, et al., A short amino acid sequence able to specify nuclear location, Cell, 39:499-509 (1984); and Steifel, et al., Expression of a maize cell wall hydroxyproline-rich glycoprotein gene in early leaf and root vascular differentiation, Plant Cell, 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, Anal. Biochem., 114:92-6 (1981).

According to a preferred embodiment, the transgenic plant provided for commercial production of foreign protein is watermelon. In another preferred embodiment, the biomass of interest is seed. For the relatively small number of transgenic plants that show higher levels of expression, a genetic map can be generated, primarily via conventional RFLP, PCR, and SSR analysis, which identifies the approximate chromosomal location of the integrated DNA molecule. For exemplary methodologies in this regard, see Methods in Plant Molecular Biology and Biotechnology, Glick and Thompson Eds., 269:284, CRC Press, Boca Raton (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR, and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

A. Genes that Confer Resistance to Pests or Disease and that Encode:

1. Plant disease resistance genes. Plant defenses are often activated by specific interaction between the product of a disease resistance gene (R) in the plant and the product of a corresponding avirulence (Avr) gene in the pathogen. A plant line can be transformed with a cloned resistance gene to engineer plants that are resistant to specific pathogen strains. See, for example, Jones, et al., Science, 266:789 (1994) (cloning of the tomato Cf-9 gene for resistance to *Cladosporium fulvum*); Martin, et al., Science, 262:1432 (1993) (tomato Pto gene for resistance to *Pseudomonas syringae* pv. tomato encodes a protein kinase); and Mindrinos, et al., Cell, 78:1089 (1994) (*Arabidopsis* RSP2 gene for resistance to *Pseudomonas syringae*).

2. A *Bacillus thuringiensis* protein, a derivative thereof, or a synthetic polypeptide modeled thereon. See, for example, Geiser, et al., Gene, 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995, and 31998.

3. A lectin. See, for example, the disclosure by Van Damme, et al., Plant Mol. Biol., 24:25 (1994), who disclose the nucleotide sequences of several *Clivia miniata* mannose-binding lectin genes.

4. A vitamin-binding protein such as avidin. See PCT Application No. US 93/06487, the contents of which are hereby incorporated by reference. The application teaches the use of avidin and avidin homologues as larvicides against insect pests.

5. An enzyme inhibitor, for example, a protease or proteinase inhibitor, or an amylase inhibitor. See, for example, Abe, et al., J. Biol. Chem., 262:16793 (1987) (nucleotide sequence of rice cysteine proteinase inhibitor); Huub, et al., Plant Mol. Biol., 21:985 (1993) (nucleotide sequence of cDNA encoding tobacco proteinase inhibitor I); and Sumitani, et al., *Biosci. Biotech. Biochem.*, 57:1243 (1993) (nucleotide sequence of *Streptomyces nitrosporeus* α-amylase inhibitor).

6. An insect-specific hormone or pheromone, such as an ecdysteroid and juvenile hormone, a variant thereof, a mimetic based thereon, or an antagonist or agonist thereof. See, for example, the disclosure by Hammock, et al., *Nature*, 344:458 (1990), of baculovirus expression of cloned juvenile hormone esterase, an inactivator of juvenile hormone.

7. An insect-specific peptide or neuropeptide which, upon expression, disrupts the physiology of the affected pest. For example, see the disclosures of Regan, *J. Biol. Chem.*, 269:9 (1994) (expression cloning yields DNA coding for insect diuretic hormone receptor) and Pratt, et al., *Biochem. Biophys. Res. Comm.*, 163:1243 (1989) (an allostatin is identified in *Diploptera puntata*). See also, U.S. Pat. No. 5,266,317 to Tomalski, et al., who disclose genes encoding insect-specific, paralytic neurotoxins.

8. An insect-specific venom produced in nature, by a snake, a wasp, etc. For example, see Pang, et al., *Gene*, 116:165 (1992), for disclosure of heterologous expression in plants of a gene coding for a scorpion insectotoxic peptide.

9. An enzyme responsible for a hyper-accumulation of a monoterpene, a sesquiterpene, a steroid, hydroxamic acid, a phenylpropanoid derivative, or another non-protein molecule with insecticidal activity.

10. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase, and a glucanase, whether natural or synthetic. See PCT Application No. WO 93/02197 in the name of Scott, et al., which discloses the nucleotide sequence of a callase gene. DNA molecules which contain chitinase-encoding sequences can be obtained, for example, from the ATCC under Accession Nos. 39637 and 67152. See also, Kramer, et al., *Insect Biochem. Mol. Biol.*, 23:691 (1993), who teach the nucleotide sequence of a cDNA encoding tobacco hornworm chitinase, and Kawalleck, et al., *Plant Mol. Biol.*, 21:673 (1993), who provide the nucleotide sequence of the parsley ubi4-2 polyubiquitin gene.

11. A molecule that stimulates signal transduction. For example, see the disclosure by Botella, et al., *Plant Mol. Biol.*, 24:757 (1994), of nucleotide sequences for mung bean calmodulin cDNA clones, and Griess, et al., *Plant Physiol.*, 104:1467 (1994), who provide the nucleotide sequence of a maize calmodulin cDNA clone.

12. A hydrophobic moment peptide. See PCT Application No. WO 95/16776 (disclosure of peptide derivatives of tachyplesin which inhibit fungal plant pathogens) and PCT Application No. WO 95/18855 (teaches synthetic antimicrobial peptides that confer disease resistance), the respective contents of which are hereby incorporated by reference.

13. A membrane permease, a channel former, or a channel blocker. For example, see the disclosure of Jaynes, et al., *Plant Sci.*, 89:43 (1993), of heterologous expression of a cecropin-β, lytic peptide analog to render transgenic tobacco plants resistant to *Pseudomonas solanacearum*.

14. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. Rev. Phytopathol.*, 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus, and tobacco mosaic virus. Id.

15. An insect-specific antibody or an immunotoxin derived therefrom. Thus, an antibody targeted to a critical metabolic function in the insect gut would inactivate an affected enzyme, killing the insect. See Taylor, et al., Abstract #497, Seventh Int'l Symposium on Molecular Plant-Microbe Interactions, Edinburgh, Scotland (1994) (enzymatic inactivation in transgenic tobacco via production of single-chain antibody fragments).

16. A virus-specific antibody. See, for example, Tavladoraki, et al., *Nature*, 366:469 (1993), who show that transgenic plants expressing recombinant antibody genes are protected from virus attack.

17. A developmental-arrestive protein produced in nature by a pathogen or a parasite. Thus, fungal endo-α-1, 4-D-polygalacturonases facilitate fungal colonization and plant nutrient released by solubilizing plant cell wall homo-α-1, 4-D-galacturonase. See Lamb, et al., *Bio/technology*, 10:1436 (1992). The cloning and characterization of a gene which encodes a bean endopolygalacturonase-inhibiting protein is described by Toubart, et al., *Plant J.*, 2:367 (1992).

18. A developmental-arrestive protein produced in nature by a plant. For example, Logemann, et al., *Bio/technology*, 10:305 (1992), have shown that transgenic plants expressing the barley ribosome-inactivating gene have an increased resistance to fungal disease.

19. Genes involved in the Systemic Acquired Resistance (SAR) Response and/or the pathogenesis-related genes. Briggs, S., *Current Biology*, 5(2) (1995).

20. Antifungal genes. See Cornelissen and Melchers, *Plant Physiol.*, 101:709-712 (1993); Parijs et al., *Planta* 183:258-264 (1991) and Bushnell et al., *Can. J. of Plant Path.* 20(2):137-149 (1998).

21. Genes that confer resistance to *Phytophthora* root rot, such as the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7 and other Rps genes. See, for example, Shoemaker et al., *Phytophthora* Root Rot Resistance Gene Mapping in Soybean, Plant Genome IV Conference, San Diego, Calif. (1995).

Any of the above listed disease or pest resistance genes (1-21) can be introduced into the claimed watermelon cultivar through a variety of means including but not limited to transformation and crossing.

B. Genes that Confer Resistance to an Herbicide:

1. An herbicide that inhibits the growing point or meristem, such as an imidazolinone or a sulfonylurea. Exemplary genes in this category code for mutant ALS and AHAS enzyme as described, for example, by Lee, et al., *EMBO 1*, 7:1241 (1988) and Miki, et al., *Theor. Appl. Genet.*, 80:449 (1990), respectively.

2. Glyphosate (resistance conferred by mutant 5-enolpyruvlshikimate-3-phosphate synthase (EPSPS) and aroA genes, respectively) and other phosphono compounds, such as glufosinate (phosphinothricin acetyl transferase (PAT), dicamba and *Streptomyces hygroscopicus* phosphinothricin-acetyl transferase PAT bar genes), and pyridinoxy or phenoxy proprionic acids and cyclohexones (ACCase inhibitor-encoding genes). See, for example, U.S. Pat. No. 4,940,835 to Shah, et al., which discloses the nucleotide sequence of a form of EPSPS which can confer glyphosate resistance. A DNA molecule encoding a mutant aroA gene can be obtained under ATCC Accession No. 39256, and the nucleotide sequence of the mutant gene is disclosed in U.S.

Pat. No. 4,769,061 to Comai. See also, Umaballava-Mobapathie in *Transgenic Research*, 8:1, 33-44 (1999) that discloses *Lactuca sativa* resistant to glufosinate. European Patent Application No. 0 333 033 to Kumada, et al., and U.S. Pat. No. 4,975,374 to Goodman, et al., disclose nucleotide sequences of glutamine synthetase genes which confer resistance to herbicides, such as L-phosphinothricin. The nucleotide sequence of a phosphinothricin-acetyl-transferase gene is provided in European Application No. 0 242 246 to Leemans, et al. DeGreef, et al., *Bio/technology*, 7:61 (1989), describe the production of transgenic plants that express chimeric bar genes coding for phosphinothricin acetyl transferase activity. Exemplary of genes conferring resistance to phenoxy proprionic acids and cyclohexones, such as sethoxydim and haloxyfop, are the Acc1-S1, Acc1-S2, and Acc1-S3 genes described by Marshall, et al., *Theor. Appl. Genet.*, 83:435 (1992).

3. An herbicide that inhibits photosynthesis, such as a triazine (psbA and gs+ genes) and a benzonitrile (nitrilase gene). Przibilla, et al., *Plant Cell*, 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes, et al., *Biochem. J.*, 285:173 (1992).

4. Acetohydroxy acid synthase, which has been found to make plants that express this enzyme resistant to multiple types of herbicides, has been introduced into a variety of plants. See Hattori, et al., *Mol. Gen. Genet.*, 246:419 (1995). Other genes that confer tolerance to herbicides include a gene encoding a chimeric protein of rat cytochrome P4507A1 and yeast NADPH-cytochrome P450 oxidoreductase (Shiota, et al., *Plant Physiol.*, 106:17 (1994)), genes for glutathione reductase and superoxide dismutase (Aono, et al., *Plant Cell Physiol.*, 36:1687 (1995)), and genes for various phosphotransferases (Datta, et al., *Plant Mol. Biol.*, 20:619 (1992)).

5. Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306, 6,282, 837, 5,767,373, and International Publication WO 01/12825.

Any of the above listed herbicide genes (1-5) can be introduced into the claimed watermelon cultivar through a variety of means including, but not limited to, transformation and crossing.

C. Genes that Confer or Contribute to a Value-Added Trait, Such as:

1. Modified fatty acid metabolism, for example, by transforming a plant with an antisense gene of stearyl-ACP desaturase to increase stearic acid content of the plant. See Knultzon et al., *Proc. Natl. Acad. Sci. USA* 89:2625 (1992).

2. Decreased phytate content—1) Introduction of a phytase-encoding gene enhances breakdown of phytate, adding more free phosphate to the transformed plant. For example, see Van Hartingsveldt et al., *Gene* 127:87 (1993), for a disclosure of the nucleotide sequence of an *Aspergillus niger* phytase gene. 2) A gene could be introduced that reduced phytate content. See Raboy et al., *Maydica* 35:383 (1990).

3. Increased sweetness of the watermelon by introducing a gene coding for monellin that elicits a flavor 100,000 times sweeter than sugar on a molar basis. See Penarrubia, et al., *Bio/technology*, 10:561-564 (1992).

4. Modified fatty acid metabolism, for example, by introducing into a plant an antisense gene of stearyl-ACP desaturase to increase stearic acid content of the plant. See Knultzon, et al., *PNAS*, 89:2625 (1992).

5. Modified carbohydrate composition effected, for example, by introducing into plants a gene coding for an enzyme that alters the branching pattern of starch. See Shiroza, et al., *J. Bacteriol.*, 170:810 (1988) (nucleotide sequence of *Streptococcus* mutants fructosyltransferase gene); Steinmetz, et al., *Mol. Gen. Genet.*, 20:220 (1985) (nucleotide sequence of *Bacillus subtilis* levansucrase gene); Pen, et al., *Bio/technology*, 10:292 (1992) (production of transgenic plants that express *Bacillus* lichenifonnis α-amylase); Elliot, et al., *Plant Mol. Biol.*, 21:515 (1993) (nucleotide sequences of tomato invertase genes); Søgaard, et al., *J. Biol. Chem.*, 268:22480 (1993) (site-directed mutagenesis of barley α-amylase gene); and Fisher, et al., *Plant Physiol.*, 102:1045 (1993) (maize endosperm starch branching enzyme II).

6. Elevated oleic acid via FAD-2 gene modification and/or decreased linolenic acid via FAD-3 gene modification. See U.S. Pat. Nos. 6,063,947; 6,323,392; and PCT Publication WO 93/11245.

D. Genes that Control Male-Sterility:

1. Introduction of a deacetylase gene under the control of a tapetum-specific promoter and with the application of the chemical N—Ac-PPT. See International Publication WO 01/29237.

2. Introduction of various stamen-specific promoters. See International Publications WO 92/13956 and WO 92/13957.

3. Introduction of the barnase and the barstar genes. See Paul, et al., *Plant Mol. Biol.*, 19:611-622 (1992).

Methods for Watermelon Transformation

Numerous methods for plant transformation have been developed, including biological and physical, plant transformation protocols. See, for example, Miki, et al., "Procedures for Introducing Foreign DNA into Plants" in *Methods in Plant Molecular Biology and Biotechnology*, Glick and Thompson Eds., CRC Press, Inc., Boca Raton, pp. 67-88 (1993). In addition, expression vectors and in vitro culture methods for plant cell or tissue transformation and regeneration of plants are available. See, for example, Gruber, et al., "Vectors for Plant Transformation" in *Methods in Plant Molecular Biology and Biotechnology*, Glick and Thompson Eds., CRC Press, Inc., Boca Raton, pp. 89-119 (1993).

A. *Agrobacterium*-Mediated Transformation:

One method for introducing an expression vector into plants is based on the natural transformation system of *Agrobacterium*. See, for example, Horsch, et al., *Science*, 227:1229 (1985); Curtis, et al., *Journal of Experimental Botany*, 45:279, 1441-1449 (1994); Tones, et al., *Plant Cell Tissue and Organ Culture*, 34:3, 279-285 (1993); and Dinant, et al., *Molecular Breeding*, 3:1, 75-86 (1997). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.*, 10:1 (1991). Descriptions of *Agrobacterium* vector systems and methods for *Agrobacterium*-mediated gene transfer are provided by Gruber, et al., supra, Miki, et al., supra, and Moloney, et al., *Plant Cell Rep.*, 8:238 (1989). See also, U.S. Pat. No. 5,591,616 issued Jan. 7, 1997.

B. Direct Gene Transfer:

Several methods of plant transformation collectively referred to as direct gene transfer have been developed as an alternative to *Agrobacterium*-mediated transformation. A generally applicable method of plant transformation is microprojectile-mediated transformation wherein DNA is carried on the surface of microprojectiles measuring 1 µm to 4 µm. The expression vector is introduced into plant tissues with a biolistic device that accelerates the microprojectiles to speeds of 300 m/s to 600 m/s which is sufficient to penetrate plant cell walls and membranes. Russell, D. R., et al., *Plant Cell Rep.*, 12 (3, January), 165-169 (1993); Aragao, F. J. L., et al., *Plant Mol. Biol.*, 20 (2, October), 357-359 (1992); Aragao, F. J. L., et al., *Plant Cell Rep.*, 12 (9, July), 483-490 (1993); Aragao, *Theor. Appl. Genet.*, 93:142-150 (1996); Kim, J., Minamikawa, T., *Plant Sci.*, 117:131-138 (1996); Sanford, et al., *Part. Sci. Technol.*, 5:27 (1987); Sanford, J. C., *Trends Biotech.*, 6:299 (1988); Klein, et al., *Bio/technology*, 6:559-563 (1988); Sanford, J. C., *Physiol. Plant*, 7:206 (1990); Klein, et al., *Bio/technology*, 10:268 (1992).

Another method for physical delivery of DNA to plants is sonication of target cells. Zhang, et al., *Bio/technology*, 9:996 (1991). Alternatively, liposome and spheroplast fusion have been used to introduce expression vectors into plants. Deshayes, et al., *EMBO J.*, 4:2731 (1985) and Christou, et al., *PNAS*, 84:3962 (1987). Direct uptake of DNA into protoplasts using $CaCl_2$) precipitation, polyvinyl alcohol, or poly-L-ornithine has also been reported. Hain, et al., *Mol. Gen. Genet.*, 199:161 (1985) and Draper, et al., *Plant Cell Physiol.*, 23:451 (1982). Electroporation of protoplasts and whole cells and tissues have also been described. Saker, M., Kuhne, T., *Biologia Plantarum*, 40(4):507-514 (1997/98); Donn, et al., In Abstracts of VIIth International Congress on Plant Cell and Tissue Culture IAPTC, A2-38, p. 53 (1990); D'Halluin, et al., *Plant Cell*, 4:1495-1505 (1992); and Spencer, et al., *Plant Mol. Biol.*, 24:51-61 (1994). See also Chupean, et al., *Bio/technology*, 7:5, 503-508 (1989).

Additional methods include, but are not limited to, expression vectors introduced into plant tissues using a direct gene transfer method, such as microprojectile-mediated delivery, DNA injection, electroporation, and the like. More preferably, expression vectors are introduced into plant tissues by using either microprojectile-mediated delivery with a biolistic device or by using *Agrobacterium*-mediated transformation. Transformed plants obtained with the protoplasm of the invention are intended to be within the scope of this invention.

Following transformation of watermelon target tissues, expression of the above-described selectable marker genes allows for preferential selection of transformed cells, tissues and/or plants, using regeneration and selection methods now well known in the art.

The foregoing methods for transformation would typically be used for producing a transgenic line. The transgenic line could then be crossed with another (non-transformed or transformed) line in order to produce a new transgenic watermelon pollenizer. Alternatively, a genetic trait which has been engineered into a particular watermelon cultivar using the foregoing transformation techniques could be introduced into another line using traditional backcrossing techniques that are well known in the plant breeding arts. For example, a backcrossing approach could be used to move an engineered trait from a public, non-elite inbred line into an elite inbred line, or from an inbred line containing a foreign gene in its genome into an inbred line or lines which do not contain that gene. As used herein, "crossing" can refer to a simple X by Y cross, or the process of backcrossing, depending on the context.

Gene Conversions

When the term "watermelon plant" is used in the context of the present invention, this also includes any gene conversions of that variety. The term "gene converted plant" as used herein refers to those watermelon plants which are developed by backcrossing, genetic engineering, or mutation, wherein essentially all of the desired morphological and physiological characteristics of a variety are recovered in addition to the one or more genes transferred into the variety via the backcrossing technique, genetic engineering, or mutation. Backcrossing methods can be used with the present invention to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8, 9, or more times to the recurrent parent. The parental watermelon plant which contributes the gene for the desired characteristic is termed the "nonrecurrent" or "donor parent." This terminology refers to the fact that the nonrecurrent parent is used one time in the backcross protocol and therefore does not recur. The parental watermelon plant to which the gene or genes from the nonrecurrent parent are transferred is known as the recurrent parent as it is used for several rounds in the backcrossing protocol. Poehlman & Sleper (1994) and Fehr (1993). In a typical backcross protocol, the original variety of interest (recurrent parent) is crossed to a second variety (nonrecurrent parent) that carries the gene of interest to be transferred. The resulting progeny from this cross are then crossed again to the recurrent parent and the process is repeated until a watermelon plant is obtained wherein essentially all of the desired morphological and physiological characteristics of the recurrent parent are recovered in the converted plant, in addition to the transferred gene from the nonrecurrent parent.

The selection of a suitable recurrent parent is an important step for a successful backcrossing procedure. The goal of a backcross protocol is to alter or substitute a trait or characteristic in the original line. To accomplish this, a gene of the recurrent cultivar is modified or substituted with the desired gene from the nonrecurrent parent, while retaining essentially all of the rest of the desired genetic, and therefore the desired physiological and morphological characteristics, watermelon line Ace Plus of the original line. The choice of the particular nonrecurrent parent will depend on the purpose of the backcross. One of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many gene traits have been identified that are not regularly selected in the development of a new line but that can be improved by backcrossing techniques. Gene traits may or may not be transgenic. Examples of these traits include, but are not limited to, male sterility, modified fatty acid metabolism, modified carbohydrate metabolism, herbicide resistance, resistance for bacterial, fungal, or viral disease, insect resistance, enhanced nutritional quality, industrial usage, yield stability, and yield enhancement. These genes are generally inherited through the nucleus. Several of these gene traits are described in U.S. Pat. Nos. 5,777,196, 5,948,957, and 5,969,212, the disclosures of which are specifically hereby incorporated by reference.

Tissue Culture

Further reproduction of the variety can occur by tissue culture and regeneration. Tissue culture of various tissues of watermelon and regeneration of plants therefrom is well known and widely published. For example, reference may be had to Sultana and Rahman, *Tissue Culture Methods of Watermelon*, (2012); Teng, et al., *HortScience*, 27:9, 1030-1032 (1992); Teng, et al., *HortScience*, 28:6, 669-1671 (1993); Zhang, et al., *Journal of Genetics and Breeding*, 46:3, 287-290 (1992); Webb, et al., *Plant Cell Tissue and Organ Culture*, 38:1, 77-79 (1994); Curtis, et al., *Journal of Experimental Botany*, 45:279, 1441-1449 (1994); Nagata, et al., *Journal for the American Society for Horticultural Science*, 125:6, 669-672 (2000); and Ibrahim, et al., *Plant Cell Tissue and Organ Culture*, 28(2), 139-145 (1992). It is clear from the literature that the state of the art is such that these methods of obtaining plants are routinely used and have a very high rate of success. Thus, another aspect of this invention is to provide cells which upon growth and differentiation produce watermelon plants having the physiological and morphological characteristics of variety Ace Plus.

As used herein, the term "tissue culture" indicates a composition comprising isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, pollen, embryos, roots, root tips, anthers, pistils, flowers, seeds, petioles, suckers, and the like. Means for preparing and maintaining plant tissue culture are well known in the art. By way of example, a tissue culture comprising organs has been used to produce regenerated plants. U.S. Pat. Nos. 5,959,185, 5,973,234, and 5,977,445 describe certain techniques, the disclosures of which are incorporated herein by reference.

Additional Breeding Methods

This invention also is directed to methods for producing a watermelon plant by crossing a first parent watermelon plant with a second parent watermelon plant wherein the first or second parent watermelon plant is a watermelon plant of watermelon line Ace Plus. Further, both first and second parent watermelon plants can come from watermelon line Ace Plus. Thus, any such methods using watermelon line Ace Plus are part of this invention: selfing, backcrosses, hybrid production, crosses to populations, and the like. All plants produced using watermelon line Ace Plus as at least one parent are within the scope of this invention, including those developed from cultivars derived from watermelon line Ace Plus. Advantageously, this watermelon cultivar could be used in crosses with other, different, watermelon plants to produce the first generation ($F_1$) watermelon hybrid seeds and plants with superior characteristics. The cultivar of the invention can also be used for transformation where exogenous genes are introduced and expressed by the cultivar of the invention. Genetic variants created either through traditional breeding methods using watermelon line Ace Plus or through transformation of watermelon line Ace Plus by any of a number of protocols known to those of skill in the art are intended to be within the scope of this invention.

The following describes breeding methods that may be used with watermelon line Ace Plus in the development of further watermelon plants. One such embodiment is a method for developing watermelon line Ace Plus progeny watermelon plants in a watermelon plant breeding program comprising: obtaining the watermelon plant, or a part thereof, of watermelon line Ace Plus, utilizing said plant or plant part as a source of breeding material, and selecting a watermelon line Ace Plus progeny plant with molecular markers in common with watermelon line Ace Plus and/or with morphological and/or physiological characteristics selected from the characteristics listed in Table 1. Breeding steps that may be used in the watermelon plant breeding program include pedigree breeding, backcrossing, mutation breeding, and recurrent selection. In conjunction with these steps, techniques such as RFLP-enhanced selection, genetic marker enhanced selection (for example, SSR markers), and the making of double haploids may be utilized.

Another method involves producing a population of watermelon line Ace Plus progeny watermelon plants, comprising crossing watermelon line Ace Plus with another watermelon plant, thereby producing a population of watermelon plants, which, on average, derive 50% of their alleles from watermelon line Ace Plus. A plant of this population may be selected and repeatedly selfed or sibbed with a watermelon cultivar resulting from these successive filial generations. One embodiment of this invention is the watermelon cultivar produced by this method and that has obtained at least 50% of its alleles from watermelon line Ace Plus.

One of ordinary skill in the art of plant breeding would know how to evaluate the traits of two plant varieties to determine if there is no significant difference between the two traits expressed by those varieties. For example, see Fehr and Walt, *Principles of Cultivar Development*, pp. 261-286 (1987). Thus the invention includes watermelon cultivar Ace Plus progeny watermelon plants comprising a combination of at least two watermelon line Ace Plus traits selected from the group consisting of those listed in Table 1, so that said progeny watermelon plant is not significantly different for said traits than watermelon line Ace Plus as determined at the 5% significance level when grown in the same environmental conditions. Using techniques described herein, molecular markers may be used to identify said progeny plant as a watermelon line Ace Plus progeny plant. Mean trait values may be used to determine whether trait differences are significant, and preferably the traits are measured on plants grown under the same environmental conditions. Once such a variety is developed, its value is substantial since it is important to advance the germplasm base as a whole in order to maintain or improve traits such as yield, disease resistance, pest resistance, and plant performance in extreme environmental conditions.

Progeny of watermelon line Ace Plus may also be characterized through their filial relationship with watermelon line Ace Plus, as for example, being within a certain number of breeding crosses of watermelon line Ace Plus. A breeding cross is a cross made to introduce new genetics into the progeny, and is distinguished from a cross, such as a self or a sib cross, made to select among existing genetic alleles. The lower the number of breeding crosses in the pedigree, the closer the relationship between watermelon line Ace Plus and its progeny. For example, progeny produced by the methods described herein may be within 1, 2, 3, 4, or 5 breeding crosses of watermelon line Ace Plus.

As used herein, the term "plant" includes plant cells, plant protoplasts, plant cell tissue cultures from which watermelon plants can be regenerated, plant calli, plant clumps, and plant cells that are intact in plants or parts of plants, such as leaves, pollen, embryos, cotyledons, hypocotyl, roots, root tips, anthers, pistils, flowers, ovules, seeds, stems, and the like.

Tables

Tables 2 and 3 show comparisons of phenotypic characteristics of watermelon line Ace Plus versus a number of commercial and experimental diploid watermelon varieties. The phenotypic data trial presented in Tables 2 and 3 was conducted at the Sakata Research Station in Woodland, Calif. Watermelon seed was sown on May 1, 2016 and transplanted to the field on May 15, 2016. Data was collected between Aug. 17, 2016 and Aug. 20, 2016. Diploid comparison varieties include experimental varieties Koufuku-1-1-1-1-1-1-1-1-1-m, SWD 8732, FWD 8704, FWD 8722 and FWD 8718 and commercial varieties Ace, SP-1, SP-6, Sidekick, Accomplice, Minipool, Mickylee, Wild Card Plus and CA9. In the Tables, an asterisk (*) indicates data not available.

TABLE 2

| VARIETY | Ace Plus | Koufuku-1-1-1-1-1-1-1-1-1-m | SWD 8732 | FWD 8704 | FWD 8722 | FWD 8718 |
|---|---|---|---|---|---|---|
| General Fruit type | Oblong, light green | Oblong | Oblong | Oblong | Oblong | Oblong |
| Adaptation | Most U.S. Areas | Most U.S. Areas | Most U.S. Areas | Most U.S. Areas | Most U.S. Areas | Most U.S. Areas |
| Relative maturity | 70 days | 70 days | 70 days | 70 days | 70 days | 70 days |
| Ploidy | Diploid | Diploid | Diploid | Diploid | Diploid | Diploid |
| Number of main stems at crown | 4 including stem holding fruit | 3 including stem holding fruit | 3 including stem holding fruit | 4 including stem holding fruit | 4 including stem holding fruit | 3 including stem holding fruit |
| Staminate flowers/plant at first fruit set | 8 | 6 | 6 | 5 | 6 | 5 |
| Stem shape | Round | Round | Round | Round | Round | Round |
| Stem diameter at 2nd node | * | 4.0 mm | 6.0 mm | 5.0 mm | 5.0 mm | 5.0 mm |
| Stem surface | Pubescent | Pubescent | Pubescent | Pubescent | Pubescent | Pubescent |
| Leaf shape | Ovate | Ovate | Ovate | Ovate | Ovate | Ovate |
| Leaf lobes | Lobed | Lobed | Lobed | Lobed | Lobed | Lobed |
| Leaf length | 18.0 cm | 16.5 cm. | 18.0 cm | 16.0 cm. | 17.0 cm | 15.0 cm |
| Leaf width | 15.0 cm | 14.0 cm | 16.0 cm | 15.0 cm | 14.0 cm | 12.0 cm |
| Leaf size | Longer than wide | Longer than wide | Longer than wide | Longer than wide | Longer than wide | Longer than wide |
| Dorsal surface pubescence | Pubescent | Pubescent | Pubescent | Pubescent | Pubescent | Pubescent |
| Ventral surface pubescence | Pubescent | Pubescent | Pubescent | Pubescent | Pubescent | Pubescent |
| Leaf color | RHS 147A (upper); RHS 147B (lower) | RHS 137B (upper); RHS 137C (lower) | RHS 137A (upper); RHS 137B (lower) | RHS 137A (upper); RHS 137B (lower) | RHS 147A (upper); RHS 147B (lower) | RHS 137A (upper); RHS 137B (lower) |
| Flower diameter across staminate | * | 3.5 cm | 3.2 cm | 4.0 cm | 3.5 cm | 3.2 cm |
| Flower color | * | RHS 4A with slight RHS 144A | RHS 4A with slight RHS 144A | RHS 4A with slight RHS 144A | RHS 4A with slight RHS 144A | RHS 4A with slight RHS 144A |
| Mature fruit shape | Oval | Oval | Oval | Oval | Oval | Oval |
| Fruit length | 16.0 cm | 12.0 cm | 15.0 cm | 17.0 cm | 17.0 cm | 18.0 cm |
| Fruit diameter at midsection | 14.0 cm | 13.0 cm | 14.0 cm | 15.0 cm | 16.0 cm | 15.0 cm |
| Avg. fruit weight | 1514 g | 806 g | 950 g | 1084 g | 1176 g | 1492 g |
| Max. fruit weight | * | 996 g | 1089 g | 1427 g | 1804 g | 1730 g |
| Fruit surface | Smooth | Smooth | Smooth | Smooth | Smooth | Smooth |
| Skin color pattern | Small stripe/mottle/net | Stripe | Stripe | Stripe | Stripe | Stripe |
| Primary color | RHS 146D | RHS 146C | RHS 146B | RHS 146C | RHS 146B | RHS 146D |
| Secondary color | RHS 146B | RHS 137A | RHS 139A | RHS 146A | RHS 139A | RHS 146B |
| Rind texture | Brittle | Brittle | Brittle | Brittle | Brittle | Brittle |
| Penetrometer reading | * | 0.80 lb. | 0.74 lb. | 1.2 lb. | 0.80 lb. | 0.98 lb. |
| Rind thickness blossom end | 5.0 mm | 5.0 mm | 1.0 mm | 2.0 mm | 2.0 mm | 2.0 mm |
| Rind thickness sides | 3.0 mm | 2.0 mm | 2.0 mm | 2.0 mm | 1.0 mm | 2.0 mm |
| Flesh texture | Soft | Soft | Soft | Soft | Soft | Soft |
| Flesh coarseness | Coarse fibrous | Coarse fibrous | Coarse fibrous | Coarse fibrous | Fine-little fiber | Coarse fibrous |
| Flesh color | RHS 179B (Greyed-red) | RHS 179B (Greyed-Red) | RHS 15B (Yellow-Orange) | RHS 179A (Greyed-Red) | RHS 18A (Yellow-Orange) | RHS 179B (Greyed-Red) |
| Seed size | Large | Medium | Medium | Medium | Small | Medium |
| Seed length | 1.2 cm | 8.0 mm | 9.0 mm | 9.0 mm | 8.0 mm | 9.0 mm |
| Seed width | 6.0 mm | 5.0 mm | 6.0 mm | 7.0 mm | 5.0 mm | 5.0 mm |
| Seed thickness | 2.0 mm | 2.0 mm | 2.0 mm | 2.0 mm | 1.0 mm | 2.0 mm |
| Number of seeds per fruit | 150 | 60 | 60 | 80 | 120 | 80 |
| Seed color | RHS 200A | RHS 166A with 202A at top | RHS 200B | RHS 200B | RHS 202A | RHS 200A |
| Known disease resistance | Fusarium wilt; Anthracnose | Untested | Untested | Untested | Untested | Untested |

TABLE 3

| VARIETY | Ace Plus | Ace | SP-1 | SP-6 | Sidekick | Accomplice | Minipool | Mickylee | Wild Card Plus | CA9 |
|---|---|---|---|---|---|---|---|---|---|---|
| General Fruit type | Oblong, light green | Oblong, gray | Round, gray | Oblong | Crimson sweet, very small | Oblong, light green | Round, gray, large | Round, gray, large | Oblong | Oblong |
| Adaptation | Most U.S. Areas | Most U.S. Areas | Most U.S. Areas | Most U.S. Areas | Most U.S. Areas | Most U.S. Areas | Most U.S. Areas | Most U.S. Areas | Most U.S. Areas | Most U.S. Areas |
| Relative maturity | 70 days | 70 days | 75 days | 70 days | 85 days | 85 days | 85 days | 90 days | 70 days | 70 days |
| Ploidy | Diploid | Diploid | Diploid | Diploid | Diploid | Diploid | Diploid | Diploid | Diploid | Diploid |
| Number of main stems at crown | 4 including stem holding fruit | 4 including stem holding fruit | 3 including stem holding fruit | 3 including stem holding fruit | 3 including stem holding fruit | 3 including stem holding fruit | 4 including stem holding fruit | 4 including stem holding fruit | 3 including stem holding fruit | 3 including stem holding fruit |
| Staminate flowers/plant at first fruit set | 8 | 8 | 6 | 6 | 6 | 6 | 4 | 5 | 6 | 6 |
| Stem shape | Round | Round | Round | Round | Round | Round | Round | Round | Round | Round |
| Stem diameter at 2nd node | * | 6.0 mm | 5.0 mm | * | 4.0 mm | 4.0 mm | 7.0 mm | 5.0 mm | * | * |
| Stem surface | Pubescent | Pubescent | Pubescent | Pubescent | Pubescent | Pubescent | Pubescent | Pubescent | Pubescent | Pubescent |
| Leaf shape | Ovate | Ovate | Ovate | Ovate | Ovate | Ovate | Ovate | Ovate | Ovate | Ovate |
| Leaf lobes | Lobed | Lobed | Lobed | Lobed | Lobed | Lobed | Lobed | Lobed | Lobed | Lobed |
| Leaf length | 18.0 cm | 18.0 cm | 20.0 cm | 17.0 cm | 16.0 cm | 15.0 cm | 17.0 cm | 19.0 cm | 18.5 cm | 17.0 cm |
| Leaf width | 15.0 cm | 15.0 cm | 17.0 cm | 15.0 cm | 12.0 cm | 14.0 cm | 9.0 cm | 12.0 cm | 16.0 cm | 15.6 cm |
| Leaf size | Longer than wide | Longer than wide | Longer than wide | Longer than wide | Longer than wide | Longer than wide | Longer than wide | Longer than wide | Longer than wide | Longer than wide |
| Dorsal surface pubescence | Pubescent | Pubescent | Pubescent | Pubescent | Pubescent | Pubescent | Pubescent | Pubescent | Pubescent | Pubescent |
| Ventral surface pubescence | Pubescent | Pubescent | Pubescent | Pubescent | Pubescent | Pubescent | Pubescent | Pubescent | Pubescent | Pubescent |
| Leaf color | RHS 147A (upper); RHS 147B (lower) | RHS 147A (upper); RHS 147B (lower) | RHS 147A (upper); RHS 147B (lower) | RHS 147A (upper); RHS 147B (lower) | RHS 137A (upper); RHS 137B (lower) | RHS 138A (upper); RHS 138B (lower) | RHS 137A (upper); RHS 137B (lower) | RHS 137A (upper); RHS 137B (lower) | RHS 147A (upper); RHS 147B (lower) | RHS 147A (upper); RHS 147B (lower) |
| Flower diameter across staminate | * | 3.5 cm | 3.8 cm | * | 2.5 cm | 2.5 cm | 3.2 cm | 3.5 cm | * | * |
| Flower color | * | RHS 1C with slight RHS 144B | RHS 1C and RHS 144B | * | RHS 4A with slight RHS 144C | RHS 4A with slight RHS 144C | RHS 4A with slight RHS 144C | RHS 1C and RHS 144B | * | * |
| Mature fruit shape | Oval | Oval | Round | Oval | Oval | Oval | Round | Round | Oval | Oval |
| Fruit length | 16.0 cm | 17.0 cm | 18.0 cm | 14.7 cm | 10.0 cm | 10.0 cm | 19.0 cm | 20.0 cm | 16.5 cm | 16.0 cm |
| Fruit diameter at midsection | 14.0 cm | 14.0 cm | 17.0 cm | 13.5 cm | 10.0 cm | 9.0 cm | 17.0 cm | 18.0 cm | 13.5 cm | 14.0 cm |
| Avg. fruit weight | 1514 g | 1768 g | 2143 g | 1357 g | 415 g | 415 g | 2464 g | 2342 g | 1512 g | 1565 g |
| Max. fruit weight | * | 2092 g | 2174 g | * | 426 g | 639 g | 2653 g | 2794 g | • | * |
| Fruit surface | Smooth | Smooth | Smooth | Smooth | Smooth | Smooth | Smooth | Smooth | Smooth | Smooth |
| Skin color pattern | Small stripe/mottle/net | Stripe | Small stripe/mottle/net | Mottle/net | Stripe | Solid | Small stripe/mottle/net | Small stripe/mottle/net | Stripe | Stripe |
| Primary color | RHS 146D | RHS 146D | RHS 146C | RHS 146B | RHS 137A | RHS 147D | RHS 145B | RHS 145D | RHS 146D | RHS 146C |
| Secondary color | RHS 146B | RHS 146A | RHS 139A | RHS 145C | RHS 146D | RHS 144B | RHS 144A | RHS 144A | RHS 146A | RHS 139A |
| Rind texture | Brittle | Brittle | Brittle | Brittle | Brittle | Brittle | Brittle | Brittle | Brittle | Brittle |
| Penetrometer reading | * | 1.0 lb. | 1.4 lb. | * | 1.8 lb. | 1.6 lb. | 2.0 lb. | 2.5 lb. | * | * |
| Rind thickness blossom end | 5.0 mm | 5.0 mm | 6.0 mm | 14.0 mm | 2.0 mm | 3.0 mm | 5.0 mm | 8.0 mm | 7.0 mm | 6.0 mm |
| Rind thickness sides | 3.0 mm | 2.0 mm | 2.0 mm | 7.0 mm | 3.0 mm | 1.0 mm | 10.0 mm | 10.0 mm | 4.0 mm | 4.0 mm |
| Flesh texture | Soft | Soft | Soft | Crisp | Crisp | Crisp | Crisp | Crisp | Soft | Soft |
| Flesh coarseness | Coarse fibrous | Coarse fibrous | Coarse fibrous | Coarse fibrous | Fine-little fiber | Fine-little fiber | Fine-little fiber | Fine-little fiber | Fine-little fiber | Coarse fibrous |
| Flesh color | RHS 179B (Greyed-red) | RHS 179B (Greyed-Red) | RHS 150D (Yellow-Green) | RHS 7C (Yellow) w/t RHS 2D | RHS 179C (Greyed-Red) | RHS 179C (Greyed-Red) | RHS 50C (Red) | RHS 42B (Red) | RHS 7A (Yellow-Green) | RHS 7B |
| Seed size | Large | Large | Large | Large | Medium | Medium | Small | Medium | Medium | Medium |
| Seed length | 1.2 cm | 11.0 mm | 10.0 mm | 11.0 mm | 10.0 mm | 10.0 mm | 8.0 mm | 8.0 mm | 9.0 mm | 8.0 mm |
| Seed width | 6.0 mm | 7.0 mm | 6.0 mm | 7.0 mm | 6.0 mm | 6.0 mm | 5.0 mm | 5.0 mm | 5.5 mm | 5.0 mm |
| Seed thickness | 2.0 mm | 2.0 mm | 2.0 mm | 2.5 mm | 2.0 mm | 2.0 mm | 2.0 mm | 1.0 mm | 1.5 mm | 1.5 mm |
| Number of seeds per fruit | 150 | 100 | 80 | 200 | 40 | 40 | 120 | 80 | 100 | 100 |

TABLE 3-continued

| VARIETY | Ace Plus | Ace | SP-1 | SP-6 | Sidekick | Accomplice | Minipool | Mickylee | Wild Card Plus | CA9 |
|---|---|---|---|---|---|---|---|---|---|---|
| Seed color | RHS 200A | RHS 200B | RHS 200A | RHS N199D | RHS N167A and RHS 202A | RHS N167A and RHS 202A | RHS 202A at edge; N199D at center | RHS 200A | RHS 200B | RHS 200A with very slight RHS 199A |
| Known disease resistance | Fusarium wilt; Anthracnose | None claimed | Co race 1 and Fon race 1, 2 | Untested | Co race 1 | Co race 1, Fon race 0, 1 | None claimed | Fon race 0 | Untested | Untested |

Table 4 shows a comparison of flower rating and fruit yield of watermelon line Ace Plus versus commercial varieties Sidekick, Ace, Minipool, Wild Card, Accomplice, SP-6 and Wild Card Plus from a trial conducted at the Sakata Research Station in Woodland, Calif. Watermelon seed was sown on Jun. 20, 2015 and transplanted to the field on Jul. 20, 2015. Plants were evaluated between Sep. 15, 2015 to Sep. 18, 2015 for flower rating and for marketable fruits. Table 4, column 1 shows the variety, column 2 shows the flower rating (scale of 1-5), column 3 shows the count of marketable fruits, column 4 shows the count of non-marketable fruits and column 5 shows the total fruit count.

TABLE 4

| Variety | Flower rating | Marketable fruits | Non-marketable fruits | Total fruit count |
|---|---|---|---|---|
| Ace Plus | 2.75 | 62 | 37 | 99 |
| Sidekick | 1.5 | 47 | 56 | 103 |
| Ace | 1.91 | 43 | 57 | 100 |
| Minipool | 3.08 | 64 | 59 | 123 |
| Wild Card | 3.16 | 58 | 41 | 99 |
| Accomplice | 2.08 | 56 | 48 | 104 |
| SP-6 | 2.91 | 46 | 58 | 104 |
| Wild Card Plus | 3.41 | 65 | 32 | 97 |

Table 5 shows a comparison of the *Fusarium* wilt (Fon 1) resistance of watermelon line Ace Plus versus similar commercial and experimental watermelon lines Ace, Sugar Baby, Charleston Gray, Calhoun Gray, SSX8493, Black Diamond, Mickylee, Crimson Sweet and All Sweet from greenhouse trials conducted at the Sakata Research Station in Fort Myers, Fla. The trials were sown on Jul. 5, 2017, inoculated with Fon1 on Jul. 12, 2017 and evaluated on Aug. 2, 2017. Data shown is an average from three repetitions. Table 5, column 1 shows the variety, column 2 shows the number of resistant plants, column 3 shows the number of intermediate resistant plants, column 4 shows the number of susceptible plants and column 5 shows the overall percent resistance to *Fusarium*. In Table 5, watermelon lines Ace and Sugar Baby are susceptible checks and watermelon lines Calhoun Gray, Charleston Gray and SSX 8493 are resistant checks.

TABLE 5

| Variety | Resistant | Intermediate | Susceptible | % Resistance |
|---|---|---|---|---|
| Ace Plus | 144 | 0 | 0 | 100% |
| Ace | 0 | 0 | 48 | 0% |
| Sugar Baby | 0 | 0 | 48 | 0% |
| Charleston Gray | 13 | 0 | 35 | 27% |
| Calhoun Gray | 48 | 0 | 0 | 100% |
| SSX8493 | 48 | 0 | 0 | 100% |
| Black Diamond | 0 | 0 | 48 | 0% |
| Mickylee | 48 | 0 | 0 | 100% |
| Crimson Sweet | 10 | 5 | 33 | 21% |
| All Sweet | 48 | 0 | 0 | 100% |

As shown in Table 5, watermelon line Ace Plus has strong resistance to *Fusarium* wilt.

Table 6 shows a comparison of the Anthracnose (Co 1) resistance of watermelon line Ace Plus versus similar commercial and experimental watermelon lines Ace (1), Sugar Baby, Charleston Gray, Black Diamond, SSBSS, SSX8493, AU-Producer, Congo, Ace (2), All Sweet, Crimson Sweet, Mickylee and Calhoun from greenhouse trials conducted at the Sakata Research Station in Fort Myers, Fla. The trials were sown on Jul. 5, 2017, inoculated with Co1 on Jul. 13, 2017 and evaluated on Jul. 27, 2017. Data shown for Ace Plus, Ace (1), Sugar Baby and Charleston Gray is from an average of five repetitions, and data shown for Black Diamond, SSBSS, SSX8493, AU-Producer, Congo, Ace (2), All Sweet, Crimson Sweet, Mickylee and Calhoun is from an average of three repetitions. Table 6, column 1 shows the variety, column 2 shows the number of resistant plants, column 3 shows the number of intermediate resistant plants, column 4 shows the number of susceptible plants and column 5 shows the overall percent resistance to Anthracnose. In Table 6, watermelon line Sugar Baby is a susceptible check and watermelon line SSX 8493 is a resistant check.

TABLE 6

| Variety | Resistant | Intermediate | Susceptible | % Resistance |
|---|---|---|---|---|
| Ace Plus | 175 | 0 | 0 | 100% |
| Ace (1) | 0 | 0 | 25 | 0% |
| Sugar Baby | 0 | 0 | 25 | 0% |
| Charleston Gray | 25 | 0 | 0 | 100% |
| Black Diamond | 0 | 0 | 30 | 0% |
| SSBSS | 30 | 0 | 0 | 100% |
| SSX8493 | 30 | 0 | 0 | 100% |
| AU-Producer | 30 | 0 | 0 | 100% |
| Congo | 30 | 0 | 0 | 100% |
| Ace (2) | 0 | 0 | 30 | 0% |
| All Sweet | 20 | 3 | 6 | 69% |
| Crimson Sweet | 30 | 0 | 0 | 100% |

TABLE 6-continued

| Variety | Resistant | Intermediate | Susceptible | % Resistance |
|---|---|---|---|---|
| Mickylee | 27 | 3 | 0 | 90% |
| Calhoun | 0 | 0 | 30 | 0% |

As shown in Table 6, watermelon line Ace Plus has strong resistance to Anthracnose.

Tables 7 and 8 show a comparison of the total number of marketable seedless triploid watermelon fruits produced using Ace Plus as the diploid pollenizer plant versus the fruit produced using experimental or commercial diploid varieties as pollenizers of field variety Secretariat. The trial was conducted at the Sakata Research Station in Woodland, Calif. Watermelon seed was sown on Jun. 20, 2015 and transplanted to the field on Jul. 20, 2015. Plants were evaluated between Sep. 15, 2015 and Sep. 18, 2015. The trial plots each had four row beds and each row had 50 Secretariat (triploid) plants. One pollenizer plant was interplanted after every five triploid plants. In total, 200 triploid Secretariat plants and 40 pollenizer plants were used for each plot. The plots were isolated and no watermelon was around it. The plots were separated from each other 300 feet apart to prevent pollen contamination among the plots. One replication was performed and the data collected included total, marketable and cull fruit count; only marketable fruits were weighed. Comparison varieties include commercial varieties Ace, Wild Card, Wild Card Plus and SP-6. Table 7, column 1 shows the variety used as the diploid pollenizer, column 2 shows the total number of fruits produced, column 3 shows the total number of marketable seedless triploid watermelon fruits produced, column 4 shows the percent of marketable fruit, column 5 shows the percent culls, and column 6 shows the total marketable fruit weight in pounds (lbs.). Table 8, column 1 shows the variety, column 2 shows the 60 count (10-13.9 lbs.) fruit number (#), column 3 shows the 60 count percent, column 4 shows the 45 count (14-17.9 lbs.) fruit number (#), column 5 shows the 45 count percent, column 6 shows the 36 count (18 lbs.—above) fruit number (#), and column 7 shows the 36 count percent.

TABLE 7

| Pollenizer | Total fruit count | Marketable fruit count | % Marketable fruit | % Culls | Total marketable fruit weight (lbs.) |
|---|---|---|---|---|---|
| Ace Plus | 572 | 347 | 60 | 40 | 5283 |
| Ace | 516 | 286 | 55 | 45 | 3978 |
| Wild Card | 614 | 382 | 60 | 40 | 5256 |
| Wild Card Plus | 598 | 401 | 67 | 33 | 5880 |
| SP-6 | 511 | 242 | 47 | 53 | 3169 |

TABLE 8

| Pollenizer | 60 count fruit # | 60 count % (10-13.9 lbs) | 45 count fruit # | 45 count % (14-17.9 lbs) | 36 count fruit # | 36 count % (18 lbs-above) |
|---|---|---|---|---|---|---|
| Ace Plus | 151 | 43% | 116 | 34% | 80 | 23% |
| Ace | 166 | 58% | 88 | 31% | 32 | 11% |
| Wild Card | 192 | 52% | 154 | 41% | 24 | 7% |
| Wild Card Plus | 176 | 43% | 142 | 36% | 83 | 21% |
| SP-6 | 167 | 69% | 67 | 28% | 8 | 3% |

As shown in Table 7, watermelon Ace Plus produced a total marketable fruit weight of 5283 pounds. As shown in Table 8, watermelon line Ace Plus produced the highest percentage of 36 count fruit (18 lbs—above) at 23%. Additionally, Ace Plus is the female parent line of Wild Card Plus, which produced the highest amount of total marketable fruit weight and a high percentage of 36 count fruit.

Table 9 shows the results from a flowering trial of watermelon line Ace Plus versus commercial varieties Ace, Wild Card, Wild Card Plus, CA9, CA9F, Mickylee, SP-6, Accomplice and Sidekick conducted at the Sakata Research Station in Fort Myers, Fla. Watermelon seed was sown on Jun. 20, 2017 and was evaluated for dates of flowering and number of flowers. Table 9, column 1 shows the variety, columns 2-21 show the dates of flowering and number of flowers for each day, and column 22 shows the total number of flowers. An asterisk (*) next to the variety name indicates that the variety did not flower during the trial.

TABLE 9

| Variety | 15-Jul. | 16-Jul. | 17-Jul. | 18-Jul. | 19-Jul. | 20-Jul. | 21-Jul. | 22-Jul. | 23-Jul. | 24-Jul. | 25-Jul. | 26-Jul. | 27-Jul. | 28-Jul. | 29-Jul. | 30-Jul. | 31-Jul. | 1-Aug. | 2-Aug. | 3-Aug. | 4-Aug. | 5-Aug. | 6-Aug. | 7-Aug. | Total |
|---|---|---|---|---|---|---|---|---|---|---|---|---|---|---|---|---|---|---|---|---|---|---|---|---|---|
| Ace Plus | 4 | 19 | 23 | 10 | 2 | 6 | | | | | | | | | | | | | | | | | | | 64 |
| Ace | | | 5 | 14 | 11 | 14 | 5 | 0 | 4 | 6 | 2 | 2 | 1 | | | | | | | | | | | | 64 |
| Wild Card | | | | | | | | | | | | | | 2 | 4 | 10 | 6 | 9 | 3 | 9 | 7 | 6 | 4 | 2 | 62 |
| Wild Card Plus | | 27 | 26 | 10 | 1 | | | | | | | | | | | | | | | | | | | | 64 |
| CA9 | | | | | | | | | 1 | | | 2 | 2 | 7 | 8 | 7 | 5 | 2 | | 2 | | 1 | 1 | | 38 |
| CA9F | | | | | | | | | | | | | | | 4 | 5 | 4 | 7 | 6 | 10 | 7 | 9 | 9 | | 61 |
| Mickylee | | 1 | 0 | 1 | 0 | 1 | 0 | 2 | 1 | 2 | 1 | 3 | 13 | 13 | 11 | 3 | 4 | 1 | | 1 | 2 | | 1 | | 61 |
| SP-6 | | | | | | | | | | | | | | 2 | | 2 | | | | 5 | | 6 | 5 | | 20 |
| Accomplice | | | | | | | | | | | | | | | | | | | | | | | 1 | | 1 |
| Sidekick* | | | | | | | | | | | | | | | | | | | | | | | | | 0 |

As shown in Table 9, watermelon line Ace Plus had earlier flowering than all other watermelon varieties tested.

Table 10 shows the results from a flowering trial of watermelon line Ace Plus versus commercial varieties Ace, Wild Card, Wild Card Plus, CA9, CA9F, SP-4, SP-6, Accomplice, Mickylee, Sidekick and Jenny conducted at the Sakata Research Station in Fort Myers, Fla. Watermelon seed was sown on Dec. 9, 2016 and was evaluated for the first date of flowering. Table 10, column 1 shows the variety, column 2 shows the company and column 3 shows the first date of flowering. An asterisk (*) next to the variety name indicates that the variety did not flower during the trial.

TABLE 10

| Variety | Company | Start flowering date |
|---|---|---|
| ACE Plus | Sakata | Jan. 2, 2017 |
| ACE | Sakata | Jan. 3, 2017 |
| Wild Card* | Sakata | |
| Wild Card Plus | Sakata | Jan. 3, 2017 |
| CA9* | Sakata | |
| CA9F | Sakata | Jan. 9, 2017 |
| SP-4* | Syngenta | |
| SP-6* | Syngenta | |
| Accomplice* | Harris Moran | |
| Mickylee | Hollar | Jan. 6, 2017 |
| Sidekick* | Harris Moran | |
| Jenny* | Nunhems | |

As shown in Table 10, watermelon line Ace Plus flowered earlier than all other watermelon varieties tested.

The use of the terms "a," "an," and "the," and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

DEPOSIT INFORMATION

A deposit of the Sakata Seed America, Inc. proprietary WATERMELON LINE ACE PLUS disclosed above and recited in the appended claims has been made with the American Type Culture Collection (ATCC), 10801 University Boulevard, Manassas, Va. 20110. The date of deposit was Aug. 28, 2018. The deposit of 2,500 seeds was taken from the same deposit maintained by Sakata Seed America, Inc. since prior to the filing date of this application. All restrictions will be irrevocably removed upon granting of a patent, and the deposit is intended to meet all of the requirements of 37 C.F.R. §§ 1.801-1.809. The ATCC Accession Number is PTA-125206. The deposit will be maintained in the depository for a period of thirty years, or five years after the last request, or for the enforceable life of the patent, whichever is longer, and will be replaced as necessary during that period.

While a number of exemplary aspects and embodiments have been discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope.

What is claimed is:

1. A seed of watermelon line Ace Plus, wherein a representative sample of seed of said line was deposited under ATCC Accession No. PTA-125206.

2. A watermelon plant, or a plant part thereof, produced by growing the seed of claim 1.

3. The plant part of claim 2, wherein said part is selected from the group consisting of a pollen, an ovule, scion, a rootstock, a fruit and a cell of the plant.

4. A tissue culture produced from protoplasts or cells from the plant of claim 2, wherein said cells or protoplasts are produced from a plant part selected from the group consisting of leaf, pollen, embryo, cotyledon, hypocotyl, meristematic cell root, root tip, pistil, anther, ovule, flower, shoot, stem, seed, and petiole.

5. A watermelon plant regenerated from the tissue culture of claim 4, wherein the plant has all of the morphological and physiological characteristics of watermelon line Ace Plus.

6. A method for producing a watermelon seed, said method comprising crossing two watermelon plants and harvesting the resultant watermelon seed, wherein at least one watermelon plant is the watermelon plant of claim 2.

7. An $F_1$ watermelon seed produced by the method of claim 6.

8. An $F_1$ watermelon plant produced by growing said seed of claim 7.

9. The method of claim 6, wherein one of said watermelon plants is watermelon line Ace Plus and the other is transgenic.

10. A method of producing an herbicide resistant watermelon plant, wherein said method comprises introducing a gene conferring herbicide resistance into the plant of claim 2, wherein the gene is selected from the group consisting of glyphosate, sulfonylurea, imidazolinone, dicamba, glufosinate, phenoxy proprionic acid, L-phosphinothricin, cyclohexone, cyclohexanedione, triazine, and benzonitrile.

11. An herbicide resistant watermelon plant produced by the method of claim 10, wherein said plant otherwise has all of the physiological and morphological characteristics of watermelon line Ace Plus.

12. A method of producing a pest or insect resistant watermelon plant, wherein said method comprises introducing a gene conferring pest or insect resistance into the plant of claim 2.

13. A pest or insect resistant watermelon plant produced by the method of claim 12, wherein said plant otherwise has all of the physiological and morphological characteristics of watermelon line Ace Plus.

14. The watermelon plant of claim 13, wherein the gene encodes a *Bacillus thuringiensis* endotoxin, and wherein said plant otherwise has all of the physiological and morphological characteristics of watermelon line Ace Plus.

15. A method of producing a disease resistant watermelon plant, wherein said method comprises introducing a gene conferring disease resistance into the plant of claim 2.

16. A disease resistant watermelon plant produced by the method of claim 15, wherein said plant otherwise has all of the physiological and morphological characteristics of watermelon line Ace Plus.

17. A method of producing a watermelon plant with a value-added trait, wherein said method comprises introducing a gene conferring a value-added trait into the plant of claim 2, and wherein said gene encodes a protein selected from the group consisting of a ferritin, a nitrate reductase, a monellin, fructosyltransferase, levansucrase, α-amylase, invertase and starch branching enzyme or encoding an antisense of stearyl-ACP desaturase.

18. A watermelon plant with a value-added trait produced by the method of claim 17, wherein said plant otherwise has all of the physiological and morphological characteristics of watermelon line Ace Plus.

19. A method of introducing a desired trait into watermelon line Ace Plus, wherein the method comprises:
(a) crossing a plant of watermelon line Ace Plus, wherein a representative sample of seed was deposited under ATCC Accession No. PTA-125206, with a plant of another watermelon cultivar that comprises a desired trait to produce progeny plants, and wherein the desired trait is selected from the group consisting of male sterility, herbicide resistance, insect or pest resistance, modified bolting and resistance to bacterial disease, fungal disease or viral disease;
(b) selecting one or more progeny plants that have the desired trait;
(c) backcrossing the selected progeny plants with watermelon line Ace Plus to produce backcross progeny plants;
(d) selecting for backcross progeny plants that have the desired trait; and
(e) repeating steps (c) and (d) two or more times in succession to produce selected third or higher backcross progeny plants that comprise the desired trait.

20. A watermelon plant produced by the method of claim 19,
wherein the plant has the desired trait and otherwise all of the physiological and morphological characteristics of watermelon line Ace Plus.

21. The watermelon plant of claim 20, wherein the desired trait is herbicide resistance and the resistance is conferred to an herbicide selected from the group consisting of glyphosate, sulfonylurea, imidazolinone, dicamba, glufosinate, phenoxy proprionic acid, L-phosphinothricin, cyclohexone, cyclohexanedione, triazine, and benzonitrile.

22. The watermelon plant of claim 20, wherein the desired trait is insect or pest resistance and the insect or pest resistance is conferred by a transgene encoding a *Bacillus thuringiensis* endotoxin.

23. A method for producing triploid, seedless watermelon fruit, wherein the method comprises the steps of:
(a) Planting a field with triploid watermelon plants;
(b) Obtaining diploid pollenizer watermelon plants for pollinizing triploid watermelon plants, wherein at least one parent of said diploid pollenizer watermelon plants is the plant of claim 2;
(c) Planting said pollenizer watermelon plants in the field of triploid watermelon plants;
(d) Allowing pollination of said triploid watermelon plants by pollen of said pollenizer watermelon plants to obtain triploid, seedless watermelon fruit; and
(e) Harvesting said triploid, seedless watermelon fruit.

24. The method for producing triploid, seedless watermelon fruit according to claim 23, wherein planting of said diploid pollenizer plants is at a ratio of approximately equal to or less than 1 diploid pollenizer watermelon plant to 3 triploid watermelon plants.

25. The method for producing triploid, seedless watermelon fruit according to claim 23, wherein planting of said diploid pollenizer plants is at a ratio of approximately equal to or less than 1 diploid pollenizer watermelon plant to 4 triploid watermelon plants.

26. The method for producing triploid, seedless watermelon fruit according to claim 23, wherein planting of said diploid pollenizer plants is at a ratio of approximately equal to or less than 1 diploid pollenizer watermelon plant to 5 triploid watermelon plants.

27. The method for producing triploid, seedless watermelon fruit according to claim 23, wherein planting of said diploid pollenizer plants is at a ratio of approximately equal to or less than 1 diploid pollenizer watermelon plant to 6 triploid watermelon plants.

28. A method for producing triploid, seedless watermelon fruit, wherein the method comprises the steps of:
(a) Inter-planting pollenizer watermelon plants and triploid watermelon plants in a field, wherein at least one parent of said pollenizer watermelon plants is the plant of claim 2; and
(b) Allowing pollination of said triploid watermelon plants by pollen of said pollenizer watermelon plants to obtain triploid, seedless watermelon fruit.

29. The method for producing triploid, seedless watermelon fruit according to claim 28, further comprising harvesting said triploid, seedless watermelon fruit.

30. A method of producing a grafted watermelon plant comprising grafting a watermelon scion onto a suitable rootstock, wherein the plant of claim 2 is used as the scion.

31. A plant of watermelon line Ace Plus, wherein a representative sample of seed of said line was deposited under ATCC Accession No. PTA-125206, wherein said plant has earlier flowering when compared to commercial inbred diploid watermelon grown in the same environment.

* * * * *